United States Patent [19]

Ishikawa

[11] 4,349,022
[45] Sep. 14, 1982

[54] MEDICAL NEEDLE ASSEMBLY

[76] Inventor: Soji Ishikawa, No. 6-22, 6-chome, Miyazaki, Takatsu-ku, Kawasaki City, Kanagawa Prefecture, Japan

[21] Appl. No.: 168,673

[22] Filed: Jul. 14, 1980

[30] Foreign Application Priority Data

Aug. 10, 1979 [JP] Japan .................. 54-109412[U]
Aug. 20, 1979 [JP] Japan .................. 54-114219[U]

[51] Int. Cl.³ ................................ A61M 5/00
[52] U.S. Cl. .................. 128/214 R; 128/348; 128/DIG. 16
[58] Field of Search ........... 128/214 R, 214.4, 221, 128/348, DIG. 16, DIG. 6

[56] References Cited

U.S. PATENT DOCUMENTS 2,928,391 3/1960 Krug .................. 128/214 R
3,769,975 11/1973 Nimoy et al. ........... 128/214.4
3,856,009 12/1974 Winnis ................. 128/214.4

Primary Examiner—Stephen C. Pellegrino
Attorney, Agent, or Firm—Armstrong, Nikaido, Marmelstein & Kubovcik

[57] ABSTRACT

A medical needle assembly for use in or with a syringe or a drip chamber liquid administration system, wherein a hollow, elongated member is loosely fitted to a flexible tube and is engageable with a needle holder element securely fitted to an injection needle so that the needle can be easily and correctly inserted into a patient's vein or the like by fitting the elongated member to the needle holder element and moving the elongated member together with the needle and the needle holder element. Upon completion of the insertion of the needle into the vein, the elongated member is detached from the needle holder element, which is thereafter secured to the patient's body skin by means of, for example, an adhesive tape.

15 Claims, 10 Drawing Figures

MEDICAL NEEDLE ASSEMBLY

FIELD OF THE INVENTION

The present invention relates in general to medical liquid dispensing devices and particularly to a needle assembly to form part of or for use in or with a medical liquid administering or blood transfusing device such as a hypodermic, intravenour or intramuscular syringe or a drip chamber liquid administering system. More particularly, the present invention is concerned with a scalp vein liquid injection device which is adapted to be fitted, when in use, to a barrel of a hypodermic, intravenous or intramuscular syringe or to a liquid conducting tube forming part of a drip chamber liquid administering system in which a liquid medicament stored in a drip chamber vessel or bottle held in a raised and vertically inverted position is to be directed into the patient's vein through the liquid conducting tube.

BACKGROUND OF THE INVENTION

A known scalp vein liquid injection device comprises a generally butterfly-shaped plastic needle holder element fixedly attached to a rear end portion of a hollow injection needle and having a pair of flexible side strip portions laterally projecting in opposite directions from the rear end portion of the needle. The rear end portion of the injection needle axially projects rearwardly from the needle holder element thus configured and is detachably fitted into a foremost end portion of a longitudinal passageway in a flexible plastic tube. The flexible plastic tube in turn is detachably fitted at the rear end thereof to an adapter element to be fitted to a front tip portion of a syringe barrel or to a leading end portion of a liquid conducting tube in a drip chamber liquid dispensing system. When in inserting the injection needle of such a scalp vein liquid injection device into a vein in, for example, a patient's arm, the flexilbe side strip portions of the needle holder element are bent into erect positions by operator's fingers and nipped between the finger tips so that the operator is able to move the needle holder element and needle together. The injection needle is thereafter inserted into the vein in the patient's arm by moving the needle holder element and needle forwardly in the axial direction of the needle. When the injection needle is thus inserted into the vein, the flexible side strip portions of the needle holder element are released from the finger tips and are allowed to resume their respective original positions projecting laterally from the rear end portion of the needle. When the side strip portions of the needle holder element assume these positions, the strip portions extend substantially in parallel with the surface of the patient's arm into which the injection needle is inserted and, thus, the needle holder element and accordingly the injection needle can be secured to the patient's arm by the use of, for example, and adjesive tape applied in part to the upper faces of the side strip portions of the needle holder element and in part to the surface of the patient's arm skin.

A scalp vein liquid injection device is thus adapted to secure an injection needle to that part of a patient's body into which the needle is inserted and is useful for proceding with medical administration or transfusion of blood for an extended period of time without constraining the subject to sit or lie in a fixed posture throughout the administration or blood transfusion.

The needle holder element of such a scalp vein liquid injection device serves not only as an anchor for the injection needle but as an aid in forcing the injection needle into a patient's vein. As the means to aid in inserting the injection needle into the vein, however, the needle holder element of the prior-art scalp vein liquid injection device has difficulties in holding the side strip portions of the needle holder element firmly and with certainty between finger tips and applying a proper concentrated force to the injection needle when in manipulating the needle holder element to insert the injection needle into the patient'vein. This is primarily because of the fact that the flexible side strip portions of the needle holder element are rather flimsy and small in construction and are inexpedient to handle.

When in inserting the injection needle of a scalp vein liquid injection device into a vein, furthermore, it is important to hold the injection needle correctly in a position in which the bevelled edge of the quillpen acuminated tip portion of the needle faces upwardly with respect to the upwardly facing surface of, for example, a patient's arm into which the injection needle is to be or has been inserted. In this instance, it is also important to have the needle holder element positioned so that the side strip portions thereof are to lie in parallel with the particular surface of the patient's arm skin when released from the finger pressure and allowed to resume their original positions and can thus be attached firmly and uniformly to the arm skin. For these purposes, not only meticulous care is required for correctly manipulating the needle holder element and needle during insertion of the injection needle into the vein but strict control over the positioning of the needle and the needle holder element to be assembled together and the quality of the resultant product during production of the scalp vein liquid injection device is indispensable.

If the injection needle fails to be inserted correctly and accurately into the desired vein by the first try, the physician (or nurse) would have to try to insert the needle into the vein repeatedly before the needle is successively inserted into the target vein, compelling the patient to suffer unnecessary pain. Such pain could however be precluded if the needle holder element of a scalp vein liquid injection device can be manipulated easily and assuredly when in inserting the injection needle into a patient's vein.

It is, accordingly, an important object of the present invention to provide an improved medical needle assembly or scalp vein liquid injection device which can be handled easily and assuredly when in inserting the injection needle into a patient's vein.

It is another important object of the present invention to provide an improved medical needle assembly or scalp vein liquid injection device which is provided with means adapted to enable the user of the device to insert the injection needle correctly and accurately into a target vein and to thereby banish the unnecessary pain which would otherwise be inflicted upon a patient when the injection needle can not successively be inserted into the target vein by the first try.

It is still another important object of the present invention to provide an improved medical needle holder assembly or scalp vein liquid injection device which requires no meticulous care for correctly positioning the needle and the needle holder element with respect to that portion of a patient's body into which the injection needle is to be inserted.

It is still another important object of the present invention to provide an improved medical needle assembly or scalp wein liquid injection device which can be manufactured without having recourse to exacting control over the relative position between the needle and the needle holder element to be assembled together and the quality of the resultant needle asssembly.

As will be understood more clearly as the description proceeds, it is still another important object of the present invention to provide an improved medical needle assembly or scalp vein liquid injection device in which the dimensions and weight of the needle holder element forming part of the needle assembly are reduced significantly so that the needle holder element can be secured to the patient's body skin by the use of an adhesive tape of a reduced size. When an adhesive tapes is attached to a body skin for an extended period of time, a rash tends to be produced on the skin by the poisoning effect of the adhesive compund. In the use of a medical needle assembly or scalp vein liquid injection device proposed by the present invention, such a problem can be to some extent alleviated because the needle holder element forming part of the needle assembly or scalp vein liquid injection device can be attached to the patient's body skin by the use of an adhesive tape of a significantly reduced size.

SUMMARY OF THE INVENTION

In accordance with the present invention and to accomplish the above described objects of the invention, there is provided a needle assembly to form part of a medical administering device such as, for example, a hypodermic, intravenous or intramuscular syringe including a syringe having a front tip portion or a drip chamber liquid administering system including a liquid conducting tube leading from a drip chamber vessel, comprising in combination a needle which is hollow throughout the axial length of the needle and which has a pointed front end portion and a rear end portion axially opposite to the front end portion, a needle holder element secured to the rear end portion of the needle, an adapter element adapted to engage the front tip portion of the aforesaid syringe barrel or a leading end portion of the aforesaid liquid conducting tube, a flexible tube detachably fitted at one end thereof to the rear end portion of the needle and at the other end thereof to the adapter element and formed with a longitudinal passageway extending throughout the length of the tube and providing communication between the needle and the adapter element, and an elongated member which is formed with an axial passageway extending throughout the length of the elongated member and having the above mentioned flexible tube loosely passed therethrough and which is engageable with the needle holder element through a front end portion of the axial bore in the tubular member.

In the needle assembly thus constructed and arranged, the needle holder element may have a generally tubular portion having the rear end portion of the needle securely passed therethrough in the axial direction of the tubular portion, wherein the aforesaid elongated member is engageable with the tubular portion of the needle holder element in the vicinity of the rear end portion of the needle.

In this instance, the needle holder element may further have a pair of flexible side strip portions laterally projecting in opposite directions from the tubular portion of the needle holder element, wherein the aforesaid elongated member is engageable with not only the tubular portion but also the above mentioned side strip portions of the needle holder element. The elongated member provided in combination with the needle holder element thus having the side strip portions in addition to the tubular portion thereof may have a front end portion formed with a pair of axial grooves which are substantially diametrically opposite to each other across the axial bore in the elongated member and which axially terminate at the foremost end of the elongated member. In this instance, the elongated member is engageable with the side strip portions of the needle holder element through the grooves, respectively, thus formed in the elongated member and is preferably formed of a non-rigid synthetic resin.

The needle holder element forming part of the needle assembly according to the present invention is formed with an axial bore extending through out the length of the needle holder element and is secured to the rear end portion of the needle through the axial bore thus formed in the needle holder element. In this instance, the needle holder element may have an axial stem portion which axially terminates at the rearmost end of the needle holder element and which is detachably inserted into the axial bore in the aforesaid elongated member. In the needle assembly having the needle holder element thus constructed and arranged may axially project from the rearmost end of the stem portion of the needle holder element and may be detachably fitted to a leading end portion of the aforesaid flexible tube. Such an elongated member is preferably formed of a rigid synthetic resin.

BRIEF DESCRIPTION OF THE DRAWINGS

The nature of and the drawbacks inherent in a prior-art medical needle assembly or scalp vein liquid injection device and the features and advantages of the medical needle assembly according to the present invention will be more clearly understood from the following description taken in conjunction with the accompanying drawings in which like reference numerals designate similar or corresponding members and elements and in which.

FURTHER DESCRIPTION OF THE PRIOR ART

Figure 1:
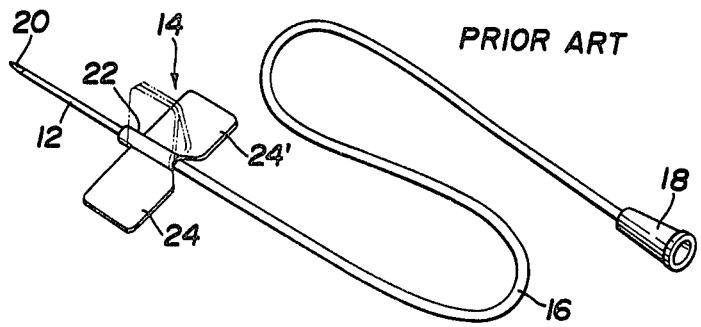
FIG. 1 is a perspective view showing a representative example of a prior-art medical needle assembly.

Referring to FIG. 1 of the drawings, a prior-art medical needle assembly is shown to be in the form of a scalp vein liquid injection device comprising an injection needle 12, a needle holder element 14, a flexible tube 16 and an adapter element 18. The injection needle 10 is hollow throughout the axial length thereof and has a pointed or quillpen acuminated front end portion 20 and a non-pointed rear end portion (not seen) axially opposite to the pointed front end portion 20. On the other hand, the needle holder element 14 has a generally tubular portion 22 formed with an axial bore through which the non-pointed rear end portion of the injection needle 12 is securely passed in the axial direction of the tubular portion 22 and axially projects outwardly from the rear end of the tubular portion 22, though not shown in FIG. 1. The needle holder element 14 further has a pair of flat side strip portions 24 and 24' laterally projecting in opposite directions from the tubular portion 22. The needle holder element 14 thus having a butterfly-shaped configuration in its entirety is formed of a non-rigid synthetic resin so that the side strip portions 24 and 24' thereof are elastically deformable from the positions laterally projecting in opposite directions from the tubular portion 20 as indicated by full lines into erect positions upstanding from the tubular portion 20 as indicated by dots-and-dash lines in FIG. 1.

The flexible tube 16 is detachably fitted at one end thereof to the adapter element 18 and at the other end thereof to the non-pointed rear end portion of the injection needle 12 axially projecting outwardly from the rear end of the tubular portion 22 of the needle holder element 14. The flexible tube 16 is formed with a longitudinal passageway extending throughout the length of the tube and providing communication between the injection needle 12 and the adapter element 18. The adapter element 18 is adapted to fit on the outer peripheral surface of the front tip portion of a syringe barrel (not shown) or to a leading end portion of a liquid conducting tube forming part of a drip chamber liquid dispensing system (not shown). In the drip chamber liquid dispensing system, a liquid medicament or blood is packed in a liquid storage bottle or bag held in a raised, vertically inverted position and is fed through the liquid conducting tube leading from the lowermost outlet end of the storage bottle or bag at a rate which is limited by, for example, a flow control clip attached to the liquid conducting tube, as is well known in the art. In the drip chamber liquid administration system using the scalp vein liquid injection device illustrated in FIG. 1, the liquid medicament or blood thus fed through the liquid conducting tube from the storage bottle or bag is directed through the adapter element 18 and the flexible tube 16 to the injection needle 12 and is administered into a patient's vein into which the injection needle 12 is inserted.

To insert the injection needle 12 into a vein in, for example, a patient's arm (not shown), the flexible side strip portions 24 and 24' are bent by operator's fingers into the erect positions indicated by the dots-and-dash lines and are nipped into contact with each other between the finger tips. The needle holder element 14 thus deformed is then moved above the surface of the patient's arm skin so that the pointed front end portion 20 of the injection needle 20 is inserted into the vein in the patient's arm. In this instance, it is important that the injection needle 12 be held in a position in which the bevelled edge of the pointed end portion 20 faces upwardly with respect to the upwardly facing surface of the patient's arm skin and that the side strip portions 24 and 24' of the needle element holder 14 be to lie in parallel with the surface of the patient's arm skin below the needle holder element 14. For this purpose, meticulous care is required for correctly manipulating the needle holder 14 and the injection needle 12 during insertion of the needle into the vein. During manufacture of the scalp vein liquid injection device, furthermore, exacting control is required in positioning the injection needle 12 and the needle holder element 14 with respect to each other, as pointed out previously. Because, furthermore, of the fact that the needle holder element 14 constructed of a non-rigid synthetic resin is rather flimsy and small in construction, it is difficult to apply a sufficient concentrated force to the injection needle 12 through the side strip portions 24 and 24' of the needle holder element 14 during insertion of the needle 12 into a vein, as also pointed out previously.

In a prior-art scalp vein liquid injection device of the nature hereinbefore described with reference to FIG. 1, difficulties have therefore been encountered in properly inserting the injection needle 12 into a desired vein and, for this reason, a patient to undergo medical administration with use of such a liquid injection device is sometimes compelled to bear unnecessary pain resulting from repeated insertion of the needle until the needle is successively inserted into a target vein. The present invention contemplates elimination of this problem which has thus far been inherent in scalp vein liquid injection devices of the type illustrated in FIG. 1.

DESCRIPTION OF THE PREFERRED EMBODIMENTS

Figure 2:
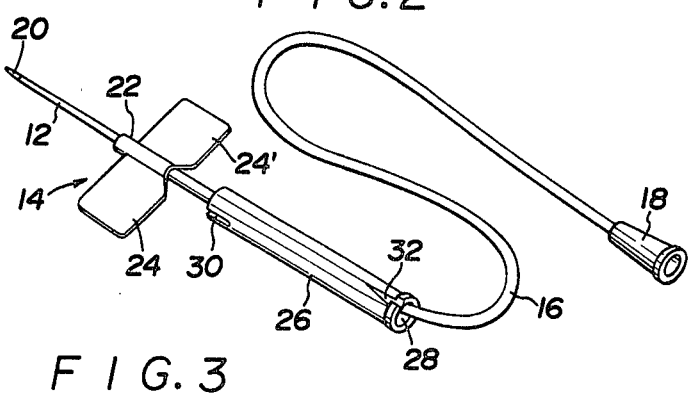
FIG. 2 is a view similar to FIG. 1 but shows a preferred embodiment of the medical needle assembly according to the present invention.

Referring to FIG. 2 of the drawings, a medical needle assembly embodying the present invention is shown to be in the form of a scalp vein liquid injection device which is constructed basically similarly to the prior-art scalp vein liquid injection device illustrated in FIG. 1. The medical needle assembly embodying the present invention is, thus, shown comprising an injection needle 12 having a pointed or quillpen acuminated front end portion 20, a generally butterfly-shaped needle holder element 14 having a tubular portion 22 and a pair of flexible side strip portions 24 and 24', a flexible tube 16, and an adapter element 18. All the above mentioned elements of the embodiment illustrated in FIG. 2 are essentially similar in configuration and function to their respective counterparts of the prior-art scalp vein liquid injection device shown in FIG. 1.

In addition to the injection needle 12, needle holder element 14, flexible tube 16 and adapter element 18, the medical needle assembly illustrated in FIG. 2 comprises an elongated, flexible tubular member 26 formed of a nonrigid synthetic resin and having an axial passageway 28 longitudinally extending throughout the length of the tubular member 26. The flexible tube 16 intervening between the injection needle 12 and the adapter element 18 is loosely passed through the axial passageway 28 in the tubular member 26 and is thus axially movable freely on the outer peripheral surface of the flexible tube 16 toward and away from the leading end of the flexible tube 16. The tubular member 26 has a front end portion formed with a pair of axial grooves or slots 30 which are substantially diametrically opposite to each other across the axial passageway 28 in the tubular member 26 and which axially terminate and open at the foremost end of the tubular member 26. The tubular member 26 further has a rear end portion formed with an axial slit 32 terminating at the rearmost end of the tubular member 26. If desired, the axial slit 26 may be slightly enlarged toward the rearmost end of the tubular member 26 so as to takes the form of a generally wedge-shaped notch. There is no limitation as to the angular position of the axial slit or notch 32 with respect to the angular positions of the axial grooves 30 and 30' about the center axis of the tubular member 26.

Figure 3:
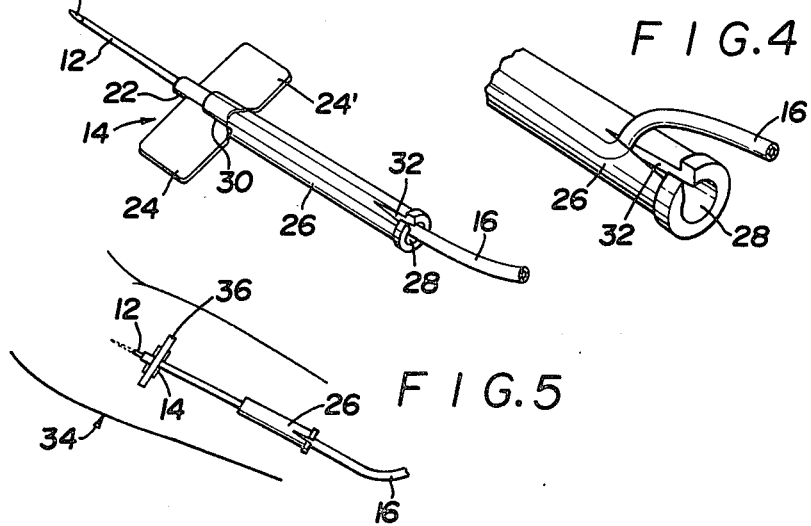
FIG. 3 is a fragmentary perspective view showing part of the needle assembly illustrated in FIG. 2, the needle assembly shown in FIG. 3 being conditioned to be ready to commence drip chamber liquid administration.
Figure 4:
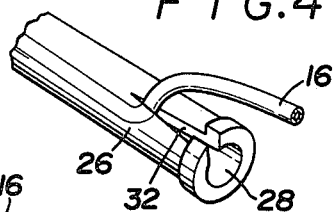
FIG. 4 is a fragmentary perspective view showing part of the needle assembly which is ready to be used for drip chamber liquid administration.

When the scalp vein liquid injection device thus constructed is to be put to use for drip chamber liquid administration, the adapter element 18 detachably fitted to the rear end portion of the flexible tube 16 is fitted to a leading end portion of a liquid conducting tube (not shown) leading from a liquid storage bottle or bag (not shown) held in a raised, vertically inverted position and having a supply of liquid medicament or blood stored therein. Before all the preparations for the administration are completed, the liquid conducting tube is fully constricted at one point thereof by means of a suitable flow control clip so as to block the communication between the storage bottle or bag. After the adapter element 18 has thus been fitted to the leading end portion of the liquid conducting tube, the tubular member 26 loosely fitted to the flexible tube 16 is axially moved toward the needle holder element 14 and is detachably fitted to the side strip portions 24 and 24' of the needle holder element 14 through the axial grooves 30 in the front end portion of the tubular member 26 as shown in FIG. 3. The tubular member 26 being thus fitted to the needle holder element 14, the tubular portion 22 of the needle holder element 14 is in part received in a front end portion of the axial passageway 28 in the tubular member 26 while the side strip portions 24 and 24' of the needle holder element 14 respectively fit in the axial grooves 30 in the front end portion of the tubular member 26, as will be seen from FIG. 3. When the tubular member 26 if fitted to the needle holder element 14 in this fashion, an axial portion of the flexible tube 16 is fitted into the axial slit or notch 32 by forcing the slit or notch 32 to expand in a circumferential direction of a rear end portion of the flexible tube 16 as will be seen from FIG. 4 so that the flexible tube 16 is retained to the tubular member 26. The injection needle 12 is now ready to be inserted into a vein in, for example, a patient's arm which is in part shown at 34 in FIG. 5.

Figure 5:
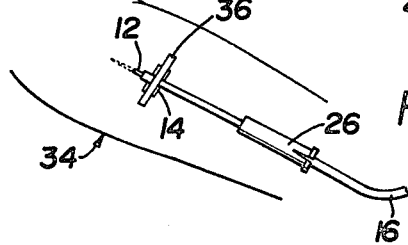
FIG. 5 is a fragmentary plan view showing part of the arrangement in which the needle assembly shown in FIG. 2 and partly in FIGS. 3 and 4 is in use for carrying out drip chamber liquid administration into a subject's arm.

To have the injection needle 12 inserted into the vein in the patient's arm 34, the tubular element 26 is nipped between the operator's finger tips and is axially moved forward to insert the needle 12 into the target vein in the patient's arm 34. After the injection needle 12 has been inserted into the vein in the patient's arm 34 in this manner, the flexible tube 16 is released from the axial slit or notch 32 in the tubular member 26, whereupon the tubular member 26 is moved rearwardly on the flexible tube 16 so as to be removed from the needle holder element 14. The tubular member 26 thus removed from the needle holder element 14 is held in a position that will not interfere with the subsequent manipulation of the needle 12 and needle holder element 14 as shown in FIG. 5. A strip 36 of adhesive tape is then applied in part to the upper faces of the needle holder element 14 and in part to the surface of the patient's arm skin so as to have the needle holder element 14 and accordingly the injection needle 12 retained to the patient's arm 34. Upon completion of the drip chamber liquid administration through the scalp vein liquid injection device thus arranged, the strip 36 of adhesive tape is stripped from the patient's arm skin and thereafter the injection needle 12 is pulled out from the patient's arm 34 by nipping the side strip portions 24 and 24' of the needle holder element 14 between finger tips and moving the needle holder element 14 rearwardly over the patient's arm 34 in a usual manner.

From the foregoing description it will have been understood that one of the outstanding advantages of the embodiment of the medical needle assembly hereinbefore described with reference to FIGS. 2 to 5 is that the injection needle 12 of the needle assembly can be inserted into a patient's vein easily and assuredly because a sufficient amount of concerntrated force can be applied to the injection needle 12 by manipulation of the tubular member 26 which has a sufficient length as compared with the needle holder element 14. Because, furthermore, of the fact that the tubular member 26 is fitted to the needle holder element 14 in such a manner as to be prohibited from turning about the center axis thereof with respect to the needle holder element 14 and the injection needle 12 during insertion of the needle 12 into the patient's vein, the angular position of the injection needle 12 and accordingly the angular position of the needle holder element 14 about the center axis of the needle 12 can be easily and accurately controlled by manipulation of the tubular member 26 when in inserting the needle 12 into the patient's vein.

Another outstanding feature of the embodiment of the medical needle assembly thereinbefore described with reference to the drawings is that the tubular member 26 has a portion of the flexible tube 16 clipped in the axial slit or notch 32 formed in the rear end portion of the tubular member 26. The tubular member 26 fitted to the needle holder element 14 is for this reason resiliently forced forward with respect to the injection needle 12 and can be stably and with certainty held to the needle holder element 14 when the injection needle 12 is being inserted into a patient's vein. The tubular member 26 can therefore be prevented from being removed from or dislodged on the needle holder element 14 during insertion of the injection needle 12 into the patient's vein even in the case where insertion of the needle 12 into the vein must be repeated a few times before the needle 12 is correctly inserted into the target vein. Because, furthermore, of the fact that the flexible tube 16 has a portion clipped and thus flattened or compressed in the axial slit or notch 32 in the tubular member 26, the axial passageway in the flexible tube 16 is closed at the flattened or compressed portion of the tube 16 so that the liquid medicament or blood which may be allowed into the flexible tube 16 from the drip chamber liquid dispensing system can be prevented from advancing beyond the constricted portion of the tube 16 during insertion of the injection needle 12 into a patient's vein.

The tubular member 26 is fitted to the flexible tube 16 usually before the flexible tube 16 is fitted to at least one of the injection needle 12 and the adapter element 18. If desired, however, the tubular member 26 may be formed with an axial slit (not shown) in its intermediate lingitudinal portion so that the flexible tube 16 fitted to the injection needle 12 and the adapter element 18 can be passed through the axial passageway 28 in the tubular member 26 through the axial slit which is made wide open by finger pressures.

Furthermore, the tubular member 26 having a circular cross section may be replaced with any elongated hollow member having an oval, rectangular or square-shaped cross section and/or may be formed with an embossed pattern or circumferential or axial projections on its outer peripheral surface so as to add to the friction between the outer peripheral surface of the tubular member 26 or the elongated hollow member and the skins of the finger tips.

If desired, the tubular member 16 may be partially or in its entirety made transparent or translucent so as to enable the user of the needle assembly to visually inspect a reverse flow of blood into a leading end portion of the passageway in the flexible tube at an incipient stage after the injection needle 12 is inserted into a patient's vein.

The first embodiment of the medical needle assembly according to the present invention is useful for eliminating most of the drawbacks which have thus far been inherent in prior-art scalp vein liquid injection devices of the described type but still has a problem in that the side strip portions 24 and 24' of the needle holder element 14 have disproportionately large areas which require a large-sized strip of adhesive strip for firmly securing the needle holder element 14 to the patient's body skin. An adhesive tape used for this purpose tends to produce a rash on the patient's body skin due to the poisoning effect of the adhesive compound and for this reason it is objectionable to use a large-sized strip of adhesive tape for securing the needle holder element 14 to the patient's body skin. The embodiment of the medical needle assembly illustrated in FIGS. 6 to 10 is useful for eliminating such a problem as well as the problems which have been encountered in prior-art scalp vein liquid injection devices.

Figure 6:
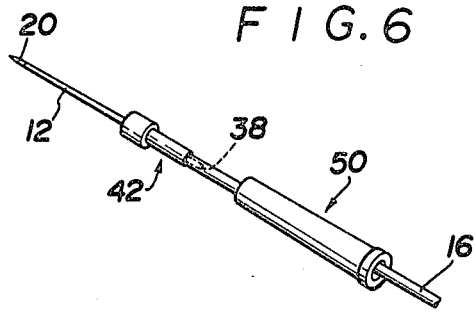
FIG. 6 is a fragmentary perspective view showing part of another preferred embodiment of the medical needle assembly according to the present invention.
Figure 7:
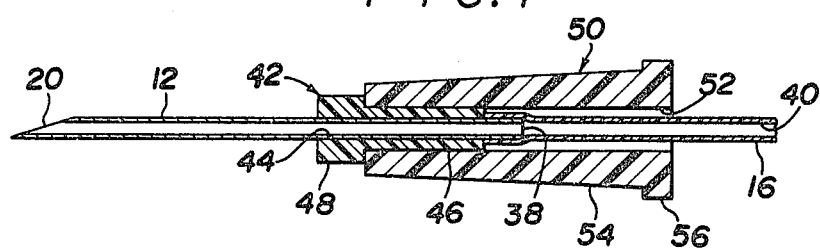
FIG. 7 is a longitudinal sectional view showing part of the needle assembly illustrated in FIG. 6, the needle assembly shown in FIG. 7 being in a condition ready for use.

Referring to FIGS. 6 and 7 of the drawings, the second embodiment of the medical needle assembly according to the present invention is also shown constructed as a scalp vein liquid injection device by way of example. In FIG. 6, the medical needle assembly embodying the present invention is, thus, shown comprising an injection needle 12 having a pointed front end portion 20 and a non-pointed rear end portion 38 and a flexible tube 16 which is formed with an axial passageway 40 (FIG. 7) extending throughout the length of the tube and which has a leading end portion detachably fitted to the non-pointed rear end portion 38 of the injection needle 12. Though not shown in FIGS. 6 and 7, the flexible tube 16 is detachably fitted at the rear end thereof to an adapter element similar to the adapter element 18 in the scalp vein liquid injection device shown in FIG. 1, thereby providing communication between the injection needle 12 and the adapter element through the axial passageway in the tube 16.

The embodiment of the medical needle assembly illustrated in FIGS. 6 and 7 further comprises an elongated needle holder element 42 formed with an axial bore 44 longitudinally extending throughout the length of the needle holder element 42. The non-pointed rear end portion 38 of the injection needle 12 is axially passed through the bore 44 thus formed in the needle holder element 42 and axially projects outwardly from the rearmost end of the needle holder element 42 into a front end portion of the axial passageway 40 in the flexible tube 16 as shown in FIG. 7. The needle holder element 42 thus fitted to the injection needle 12 has a cylindrical stem portion 46 axially terminating at the rearmost end of the needle holder element 42 and a flanged axial end portion axially projecting forwardly from the stem portion 46 toward the pointed end portion 20 of the injection needle 12 and formed with an annular outer flange 48 adjacent the foremost end of the needle holder element 42. The needle holder element 42 is preferably formed of a non-rigid synthetic resin.

The embodiment shown in FIGS. 6 and 7 further comprises an elongated tubular member 50 formed with an axial passageway 52 longitudinally extending throughout the length of the member 50 and having a diameter which is substantially equal to or slightly larger than the outside diameter of the stem portion 46 of the needle holder element 42. The relationship between the axial length of the tubular menber 50 and the axial length of the stem portion 46 of the needle holder element 42 is such that the length of the stem portion 46 is appreciably less than the length of the length of the axial passageway in the tubular member 50 so that the tubular member 50 can be easily fitted to and removed from the stem portion 46 of the needle holder element 42 and can nevertheless firmly and stably held on the stem portion 46 of the needle holder element 42 once attached thereto. The tubular member 50 has a stem portion 54 axially terminating at the rearmost end of the tubular member 50 and a flanged rear end portion axially projecting rearwardly from the stem portion 54 and having an annular outer flange 56 adjacent the rearmost end of the tubular member 50. The stem portion 52 of the tubular member 50 preferably has a frusto-conical configuration tapered from the flange 56 toward the rearmost end of the tubular member 50 as shown. When the tubular member 50 thus shaped is fitted onto the needle holder element 42, the tubular member 50 has its annular rear end face held in contact with the axially inner end face of the flange 48 of the needle holder element 42 as illustrated in FIG. 7. The tubular member 50 is preferably constructed of a rigid synthetic resin and may have formed on the outer peripheral surface of the stem portion 54 an embossed pattern or a plurality of discrete projections (not shown) so as to add to the friction between the outer peripheral surface of the stem portion 54 and the skins of the user's finger tips during manipulation of the tubular element 50. The above mentioned projections which may thus be formed on the outer peripheral surface of the stem portion 54 may be arranged to extend circumferentially of the stem portion 54 or may be elongated longitudinally of the stem portion 54 and substantially equiangularly spaced apart from each other about the center axis of the tubular member 50. As an alternative, the discrete projections may be dotted over the outer peripheral surface of the stem portion 54. For the same reason as previously explained in connection with the tubular member 26 in the first embodiment of the present invention, the tubular member 50 of the second embodiment may also partially or in its entirety formed of a transparent or translucent material.

In order that the scalp vein liquid injection device thus constructed be put to use for drip chamber liquid administration for a patient, the tubular element 50 is first fitted to the flexible tube 16 by passing the flexible tube 16 through the axial passsageway 52 in the tubular member 50 with the reduced end of the tapered stem portion 54 of the tubular member 50 directed toward the leading end of the flexible tube 16. The flexible tube 16 is thereafter detachably fitted at its leading end to the non-pointed rear end portion 38 of the injection needle 12 and at the rear end thereof to the previously mentioned adapter element (indicated at 18 in FIGS. 1 and 2). It is, in this instance, apparent that the tubular element 50 may be fitted to the flexible tube 16 after the flexible tube 16 has been fitted to one of the injection needle 12 and the adapter element. The adapter element forming part of the scalp vein liquid injection device thus completed is attached to a leading end portion of a liquid conducting tube (not shown) leading from a liquid storage bottle or bag (not shown) having stored therein a suitable liquid medicament or blood and held in a raised, vertically inverted position.

The liquid conducting tube at this stage is clipped at a suitable point thereof so that the liquid medicament or blood which may be allowed into the tube from the storage bollte or bag is not permitted to reach the leading end of the tube.

The tubular member 50 is then fitted to the needle holder element 42 by manipulating the needle holder element 42 and the tubular member 50 so that the stem portion 46 of the former is inserted into the axial passageway 52 in the latter from the foremost end of the passageway 52. The tubular member 50 being thus fitted to the needle holder element 42, the flexible tube 16 fitted to the non-pointed rear end portion 38 of the injection needle 12 extends through a rear half of the axial passageway 52 in the flexible tube 16 as shown in FIG. 7.

Figure 8:
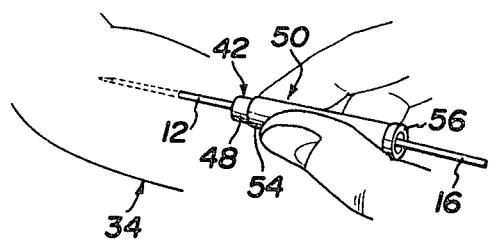
FIG. 8 is a fragmentary perspective view showing part of the arrangement in which the injection needle forming part of the needle assembly partly illustrated in FIGS. 6 and 7 is being inserted into a subject's arm.
Figure 9:
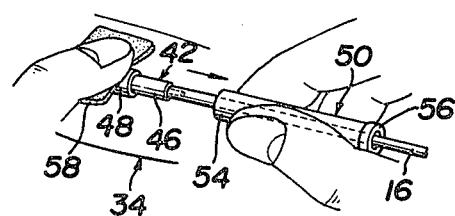
FIG. 9 is a view similar to FIG. 8 but shows the condition in which the needle assembly is being manipulated to be ready to carry out drip chamber liquid administration into the subject's arm.
Figure 10:
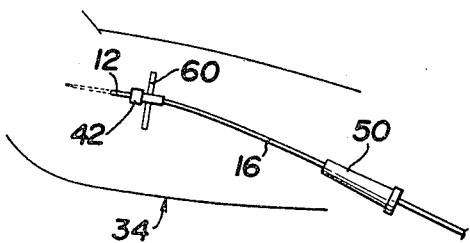
FIG. 10 is a fragmentary plan view showing part of the arrangement in which the needle assembly partly illustrated in FIGS. 6 to 9 is in use for drip chamber liquid administration in to the subject's arm.

The injection needle 12 is thereafter inserted into a vein in, for example, the patient's arm (indicated in part at 34 in FIGS. 8 and 9 by holding the stem portion 54 of the tubular member 50 between finger tips and axially moving the tubular member 50 forwardly over the patient's arm 34 as shown in FIG. 8. After the injection needle 12 has thus been inserted into the patient's vein, a suitable sterilized material such as a sheet of alcohol-impregnated cotton 58 is applied to an upper portion of the flange 48 of the needle holder element 42 and the tubular member 50 is pulled away from the flange 48 of the needle holder element 42 by, for example, right-hand fingers while softly pressing the flange 48 against the patient's arm skin through the sheet 58 of cotton by, for example, a left-hand finger for thereby removing the tubular member 50 from the needle holder element 42 as shown in FIG. 9. The tubular member 50 thus released from the needle holder element 42 is detained in a position that will not interfere with the subsequent manipulation of the needle 12 and the needle holder element 42. The needle holder element 42 is thereafter secured to the patient's arm skin by means of a narrow strip 60 of adhesive tape applied in part to an upper portion of the outer peripheral surface of the stem portion 46 of the needle holder element 42 and in part to the patient's arm skin as illustrated in FIG. 10. The scalp vein liquid injection device is now in order for carrying out the drip chamber liquid administration for the patient.

As will have been understood from the foregoing description, one of the outstanding features of the embodiment of the invention hereinbefore described with reference to FIGS. 6 to 10 of the drawings is that the needle holder element 42 is devoid of the side strip portions 24 and 24' which form part of the needle holder element in the prior-art scalp vein liquid injection device illustrated in FIG. 1 or the embodiment of the present invention illustrated in FIGS. 2 to 5. The needle holder element 50 in the embodiment of FIGS. 6 to 10 can therefore be fitted to the injection needle 12 without considering the angular relationship between the needle 12 and the needle holder element 42 about the center axis of the needle 12.

Another outstanding feature of the second embodiment of the present invention is that the injection needle 12 of the needle assembly can be inserted into a patient's vein easily and assuredly because a sufficient amount of concentrated force can be applied to the injection needle 12 by manipulating the tubular member 50 fitted to the needle holder element 42. The injection needle 12 can therefore be correctly and accurately into a desired vein without compelling the patient to bear unnecessary pains resulting from a failure in inserting the needle 12 successively into the target vein by the first try.

The annular outer flange 48 of the needle holder element 42 in the second embodiment of the present invention serves not only as stop means effective to dictate the length in which the tubular member 50 is to be fitted to the needle holder element 42 but as a rest onto which a finger pressure is to be applied when in pressing the needle holder element 42 against a patient's body skin and concurrently pulling the tubular member 50 from the portion 46 of the needle holder element 42 upon completion of the insertion of the injection needle 12 into a patient's vein.

Still another outstanding feature of the embodiment of FIGS. 6 to 10 is that the needle holder element 42 to be held attached to a patient's body skin for an extended period of time until a medical administering operation for the patient is less massive and smaller in size than the needle holder element 14 having the side strip portions 24 and 24' as in the prior-art device illustrated in FIG. 1 or the first embodiment of the present invention shown in FIG. 2. For this reason, the needle holder element 42 can be secured to the patient's body skin by the use of a sufficiently small-sized strip of adhesive tape which will significantly lessen the risk of producing a rash on the patient's body skin to which the adhesive tape is to be applied.

When, furthermore, the tubular member 50 is made at least in part transparent or translucent as previously mentioned, the user of the scalp vein liquid injection device is enabled to visually inspect a reverse flow of blood into a leading end portion of the flexible tube 16 at an incipient stage after the injection needle is inserted into a patient's vein.

While each of the embodiments herein shown has been assumed to be used for drip chamber liquid administration for a patient, it will be apparent that the medical needle assembly can be used not only for such a purpose but with a usual syringe including a syringe barrel having a front tip portion. In this instance, the adapter element fitted to the rear end of the flexible tube forming part of the needle assembly is detachably fitted to the front tip portion of the syringe barrel so that constant communication is established between the passageway in the flexible tube and the liquid chamber in the syringe barrel as will be readily understood by those skilled in the art.

What is claimed is:

1. A needle assembly to form a part of a medical administering device such as a syringe including a syringe barrel having a front tip portion or a drip chamber liquid administering system including a liquid conducting tube leading from a drip chamber vessel, comprising in combination a needle which is hollow throughout the axial length of the needle and which has a pointed front end portion and a rear end portion axially opposite to the front end portion, a needle holder element secured to the rear end portion of the needle, an adapter element adapted to engage the front tip portion of said syringe barrel or a leading end portion of said liquid conducting tube, a flexible tube detachably fitted at one end thereof to the rear end portion of said needle and at the other end thereof to said adapter element and formed with a longitudinal passageway extending throughout the length of the tube and providing communication between said needle and said adapter element, and an elongated member which is formed with an axial passageway extending throughout the length of the elongated member and having said flexible tube loosely passed therethrough and which is engageable with said needle holder element through a front end portion of the axial bore in the elongated member, said needle holder element having a generally tubular portion having the rear end portion of the needle securely passed therethrough in the axial direction of the tubular portion and said elongated member being engageable with said tubular portion of the needle holder element in the vicinity of the rear end portion of said needle, said needle holder element further having a pair of flexible side strip portions laterally projecting in opposite directions from said tubular portion of the needle holder element and said elongated member being engageable with said side strip portions as well as said tubular portion of the needle holder element, wherein said elongated member has a front end portion formed with a pair of axial grooves which are substantially diametrically opposite to each other across the axial bore in the elongated member and which axially terminate at the foremost end of the elongated member, the elongated member being engageable with said side strip portions of the needle holder element through said grooves, respectively.

2. A needle assembly as set forth in claim 1, in which said needle holder element is formed with an axial bore extending throughout the length of the needle holder element and is secured to the rear end portion of the needle through the axial bore in the needle holder element.

3. A needle assembly as set forth in claim 1, in which said elongated member has a rear end portion formed with an axial slit terminating at the rearmost end of the elongated member, said axial slit being adapted to be opened out for receiving a portion of said flexible tube and thereby releasably retaining the flexible tube to the elongated member.

4. A needle assembly as set forth in claim 1 or 3, in which said elongated member is formed of a non-rigid synthetic resin.

5. A needle assembly as set forth in claim 1 or 3, in which said elongated member is at least in part constructed of a non-opaque material.

6. A needle assembly as set forth in claim 1 or 3, in which said elongated member is formed of a non-opaque, non-rigid synthetic resin.

7. A needle assembly as set forth in claim 1 or 3, in which said elongated member has a generally circular external cross section.

8. A needle assembly as set forth in claim 1 or 3, in which said elongated member has a generally oval external cross section.

9. A needle assembly as set forth in claim 1 or 3, in which said elongated member has a generally rectangular external cross section.

10. A needle assembly as set forth in claim 1 or 3, in which said elongated member has a generally square-shaped external cross section.

11. A needle assembly as set forth in claim 1 or 3, in which said elongated member has an outer peripheral surface formed with an embossed pattern.

12. A needle assembly as set forth in claim 1 or 3, in which said elongated member has an outer peripheral surface formed with a plurality of discrete projections.

13. A needle assembly as set forth in claim 12, in which said projections extend in axial directions of said elongated member.

14. A needle assembly as set forth in claim 12, in which said projections extend circumferentially of the outer peripheral surface of said elongated member.

15. A needle assembly as set forth in claim 1 or 3, in which said elongated member has an axial slit in its intermediate longitudinal portion.

* * * * *